United States Patent [19]

Fujiwara et al.

[11] Patent Number: 5,143,935
[45] Date of Patent: Sep. 1, 1992

[54] BENZAMIDE DERIVATIVES

[75] Inventors: Hiromichi Fujiwara; Akihiko Ogawa; Hideyo Sakiyama; Toshiaki Tamura, all of Hyogo, Japan

[73] Assignee: Teikoku Chemical Industry Co., Ltd., Osaka, Japan

[21] Appl. No.: 777,011

[22] Filed: Oct. 16, 1991

[30] Foreign Application Priority Data

Oct. 16, 1990 [JP] Japan ................... 2-277976

[51] Int. Cl.$^5$ ................. A61K 31/40; C07D 207/04
[52] U.S. Cl. ................................ 514/426; 548/557
[58] Field of Search ...................... 548/557; 514/426

[56] References Cited

U.S. PATENT DOCUMENTS 4,143,150 3/1979 Welstead, Jr. et al. ............ 548/557

Primary Examiner—Mary C. Lee
Assistant Examiner—Joseph K. McKane
Attorney, Agent, or Firm—Wenderoth, Lind & Ponack

[57] ABSTRACT

A benzamide derivative represented by the formula:

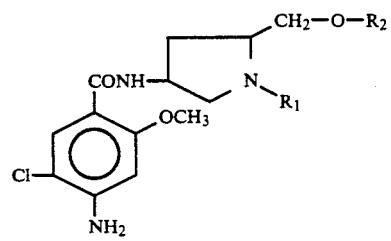

having a promoting activity of gastrointestinal tract and pharmacentical composition containing the same.

5 Claims, No Drawings

BENZAMIDE DERIVATIVES

FIELD OF THE INVENTION

The present invention relates to a class of novel benzamide derivatives each having a promoting activity to gastrointestinal tract.

BACKGROUND OF THE INVENTION

4-Amino-5-chloro-N-((2-diethylamino) ethyl)-2-methoxy benzamide (common name: Metoclopramide) is a well-known compound having a promoting activity to gastrointestinal tract and especially to stomach, and (±) 4-amino-5-chloro-N-(3R*,4S*)-1-(3-(p-fluorophenoxy)propyl)-3-methoxy-4-piperidyl)-o-anisamide (common name: Cisapride) is a well-known gastrokinetic compound customarily used for the treatment of chronic gastrics, syndrome of gastrointestinal tract accompanied with postgastrectomy, regurgitant esophagitis and suprious obstipation. Metoclopramide has, however, undesired properties of inducing exstrapyramidal syndrome and other undesired syndrome; due to its specific activity toward central nervous system. Recently, Cisapride has also been reported to have undesired properties of inducing exstrapyramidal syndrome and especially parkinsonism.

Under the circumstances, it has long been desired to have a new medicinal compound which is excellent in absorption through gastrointestinal tract and has the least activity toward central nervous system.

It is, therefore, an object of the invention to provide a novel class of compounds having no or substantially no activity toward central nervous system and having an excellent promoting activity to digestive tract and especially to stomach.

An additional object of this invention is to provide a pharmacentical composition comprising such novel compound or its phamacentically acceptable salt and other additives or carriers.

SUMMARY OF THE INVENTION

According to the invention, the abovementioned object can be attained with a novel class of benzamide derivatives represented by the formula:

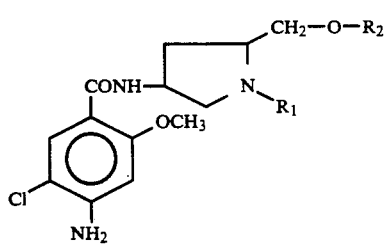

(I)

in which $R_1$ is hydrogen atom, lower alkyl, halogen substituted lower alkyl or aralkyl group; $R_2$ is hydrogen atom or lower alkyl group.

The present benzamide derivatives may be advantageously prepared as follows:

That is, 4-amino-5-chloro-2-methoxy benzoic acid is reacted with a compound of the formula:

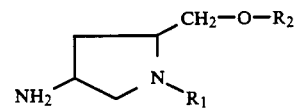

(IV)

This reaction may be preferably carried out in the presence of such condensing agent as N,N'-dicyclohexyl carbodiimide (DCC), 1,1'-sulfinyl imidazole, 1,1'-carbonyl diimidazole or the like, or by using a reactive derivative of 4-amino-5-chloro-2-methoxy benzoic acid as, for example, acid halide, active ester, acid anhydride and the like.

As a reaction medium, any of the solvent which are inert to the abovementioned reaction may be satisfactorily used, including tetrahydrofuran, dioxane, benzene, toluene, petroleum hydrocarbons as hexane, octane, petroleum benzine and the like, dimethyl formamide, pyridine, triethylamine, acetonitrile, chloroform and the like, which are inert to an amine and an acylation reagent.

At the time when an acid halide is used as a starting material, the reaction may be advantageously promoted by the co-presence of a tertiary amine as pyridine, triethylamine, dimethyl aniline and the like. Since there are two asymmetric carbons at 3 and 5 positions (or 2 and 4 positions) in pyrrolidine ring of said compound (IV), there are four stereoisomers each having different stereostructure in said compound (IV). These four are all included in the present objective compounds.

The present compounds do possess nitrogen atoms and hence, may form addition salts with various acids. Therefore, any of the pharmaceutically acceptable addition salts as salts with such mineral acids as hydrochloric acid, sulfuric acid, hydriodic acid hydrobromic acid, carbonic acid and the like, and with such organic acids as methane sulfonic acid, toluene sulfonic acid, benzene sulfonic acid, lactic acid, succinic acid, tartaric acid, fumaric acid, citric acid and the like may also be included in the objective compounds.

Thus obtained compounds of the present invention are characterized in that they have excellent promoting activities to digestive tract and especially to stomach, but no or substantially no activities toward central nervous system.

The present compound may be formulated, together with other additives or carriers, to any of the forms adapted to easy application as, for example, tablet, capsule, granule, solution and the like and however, preference is given to orally administrative forms because of application easiness.

For example, tablets may be advantageously prepared by mixing the present compound or its salt well with vehicles (as lactose, glucose, starch, crystalline cellulose and the like), binders (as starch solution, hydroxy propyl cellulose solution, carboxy methyl cellulose solution and the like), disintegrators (as carboxy methyl cellulose calcium, carboxy methyl cellulose, low-substituted hydroxy propyl cellulose and the like) and the like, adding with lubricants (as magnesium stearate, purified talc, calcium stearate and the like), and subjecting to tableting machine.

Daily dosage may be 0.05-1.0 mg/kg, preferably 0.1 to 0.5 mg/kg, depending on symptom, which may be administered in one time or separately in 2 or more applications. Appropriate dosage may be determined by due consideration of individual response to the active substance, application period, symptom and the like.

The present compounds have been evaluated by the following methods:

(1) Promoting activity to gastric emptying:

To a group of mice (average body weight:about 20 g), an aqueous solution of the compound obtained in the respective Example was orally administered at 3 mg/kg and after 30 minutes later, 0.1 ml of aqueous 1.5% carboxymethyl cellulose solution containing 0.05% phenol red was orally administered. After leaving for 15 minutes, stomach was extracted and the phenol red amount remaining in the stomach was measured to determine the excreting activity for the tested compound.

As a control, the similar experiment as mentioned hereinabove was repeated excepting omitting the oral administration of the test compound. Instead of this, water was administered.

Promoting activity percentage was calculated from the following equation:

$$\text{Promoting activity \%} = \left( \frac{\text{excreting activity in the animal administered with test compound} - \text{excreting activity in control}}{\text{excreting activity in control}} \right) \times 100$$

(2) Activity to Apomorphine induced vomiting:

Top a group of mongrel dogs (average body weight: about 10 kg), an aqueous solution of the compound obtained in the respective Example was administered at 0.1 mg/kg by a subcutaneous administration rout, and after 30 minutes later, 0.1 mg/kg of Apomorphine was subcutaneously administered.

Time duration up to the appearance of vomiting (the latent period in hour), vomiting frequency and vomiting lasting time were determined and used as measures for evaluating the activity. In the control, a physiological saline was subcutaneously administered in place of the aqueous solution of test compound.

The invention shall be now more fully explained in the following Examples.

EXAMPLE 1

Into a reaction vessel, were placed 1.00 g of 4-amino-5-chloro-2-methoxy benzoic acid, 0.75 g of 3-amino-1-ethyl-5-hydroxymethyl pyrrolidine, 0.83 g of 1-hydroxy-1H-benzotriazole monohydrate, 1.13 g of dicyclohexyl carbodiimide (DCC), 15 ml of tetrahydrofuran (THF) and 2 ml of dimethyl formamide (DMF), and thus obtained mixture was stirred at room temperature for 14 hours. Thereafter, the precipitated dicyclohexyl carbonyl urea (DCU) was removed off, the filtrate was concentrated under reduced pressure and the residue was added with a dilute hydrogen chloride solution and washed twice with chloroform. The aqueous solution was alkalized with sodium bicarbonate and then extracted twice with chloroform. The organic extract was washed with a saturated aqueous saline solution and dried over magnesium sulfate. The extract was concentrated under reduced pressure and the residue was added with toluene, from which crystalline material was precipitated and separated. This was treated in isopropyl alcohol with HCl gas to convert to its hydrochloride and the thus formed hydrochloride precipitate was separated to obtain 1.05 g of 4-amino-5-chloro-2-methoxy-N-(1-ethyl-5-hydroxymethyl pyrrolidin-3-yl) benzamide hydrochloride (Compound of Example 1 in Table 1) M.p. 162° to 165° C.

NMR spectrum (DMSO-d$_6$)δ(TMS, ppm): 1.28 (3H,t) 1.6–4.1 (9H), 3.85 (3H,s ), 4.4–5.1 (4H), 6.53 (1H, s), 7.70 (1H, s), 8.30 (1H, d), 10.7 (1H, broad).

EXAMPLES 2 TO 9

Using the similar procedures as stated in Example 1, excepting the substituted groups $R_1$, $R_2$ in the general formula I were specifically determined the hydrochloride compounds of Examples 2 to 9 in Table 1 were obtained, respectively.

EXAMPLE 2

$R_1 = CH_2CH_2CH_3$, $R_2 = H$) M.p. 171°–174° C.

NMR spectrum (DMSO-d$_6$)δ(TMS, ppm): 0.90 (3H,t), 1.3–4.3 (11H), 3.85 (3H,s ), 4.7 (1H, broad), 5.2–6.2 (3H), 6.50 (1H, s), 7.67 (1H, s), 8.3 (1H, d), 10.6 (1H, broad),

EXAMPLE 3

$R_1 = CH(CH_3)_2$, $R_2 = H$, M.p. 198°–204° C.

NMR spectrum (DMSO-d$_6$)δ(TMS, ppm): 1.27 (3H,d), 1.37 (3H, d), 1.5–2.3 (1H), 2.8–4.0 (7H), 3.88 (3H, s), 4.7 (1H, broad), 5.5 (1H, broad), 5.9 (2H, broad)6.55 (1H, s), 7.75 (1H, s), 8.40 (1H, d), 10.8 (1H, broad).

EXAMPLE 4

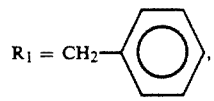

$R_2 = H$ M.p. 128°–134° C.

NMR spectrum (DMSO-d$_6$)δ(TMS, ppm): 1.6–4.9 (10H), 3.83 (3H, s), 5.6 (1H, broad). 5.9 (2H, s), 6.50 (1H, s), 7.3–7.8 (5H), 7.67 (1H, s), 8.3 (1H, d), 11.1 (1H, broad).

EXAMPLE 5

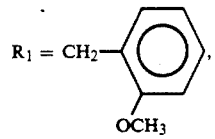

$R_2 = H$ Glassy product,

NMR spectrum (DMSO-d$_6$)δ(TMS, ppm): 1.7–5.6 (16H), 5.17 (3H, s), 6.56 (1H, s), 6.7–8.0 (4H), 7.73 (1H, s), 8.40 (1H, d), 10.5 (1H, broad).

EXAMPLE 6

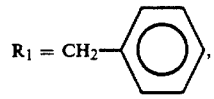

$R_2 = CH_3$ Glassy product,

NMR spectrum (DMSO-d$_6$)δ(TMS, ppm): 1.6–5.2 (11H), 3.33 (3H, s), 3.90 (3H,s ), 6.40 (2H, s), 6.57 (1H, s), 7.2–7.9 (5H), 7.70 (1H, s), 8.37 (1H, d), 11.93(1H, broad).

EXAMPLE 7

$R_1=CH(C_6H_5)_2$, $R_2=H$ M.p. 215°–219° C.

NMR spectrum (DMSO-$d_6$)$\delta$(TMS, ppm): 1.8–4.1 (8H), 3.85 (3H,s) 4.4–5.5 (3H), 5.9 (1H, broad), 6.53 (1H, s), 7.0–8.3 (10H), 7.70 (1H, s), 8.40 (1H, d), 11.5 (1H, broad).

EXAMPLE 8

$R_1=CH_3$, $R_2=H$ M.p. 119°–122° C.

NMR spectrum (DMSO-$d_6$)$\delta$(TMS, ppm): 1.6–5.3 (8H), 2.90 (3H, d), 3.90 (3H, s), 5.77 (3H, s), 6.63 (1H, s), 7.73 (1H, s), 8.33 (1H, d), 10.8 (1H, broad).

EXAMPLE 9

$R_1=CH_2CH_2F$, $R_2=H$ M.p. 170°–172° C.

NMR spectrum (DMSO-$d_6$)$\delta$(TMS, ppm): 1.5–5.8 (12H), 3.85 (3H, s), 5.50 (3H,s), 6.55 (1H, s), 7.70 (1H, s), 8.4 (1H, d), 10.7–11.5 (1H, broad).

EXAMPLE 10

Into a solution of 1.4 g of 4-amino-5-chloro-2-methoxy-N-(1-diphenylmethyl-5-hydroxymethyl pyrrolidin-3-yl) benzamide hydrochloride (Compound of Example 7) in methanol, 0.28 g of 5% palladium/carbon was added and hydrogenation was effected under normal pressure and temperature conditions. At the stage when 63 ml of hydrogen were consumed, the hydrogenation was discontinued and the reaction mixture was filtered to remove the catalyst and then concentrated under reduced pressure to precipitate crystals. The separated crystals were dispersed in aceton and filtered. Thus obtained crude product was recrystallized from ethanol to obtain 0.46 g of 4-amino-5-chloro-2-methoxy-N-(5-hydroxymethyl pyrrolidin 3-yl) benzamid hydrochloride (Compound of Example 10 in Table 1):

$R_1=H$, $R_2=H$ M.p. 220°–223° C.

NMR spectrum (DMSO-$d_6$)$\delta$(TMS, ppm): 1.5–4.0 (7H), 3.83 (3H, s), 4.6 (1H,broad), 5.5 (1H, broad), 5.9 (2H, broad), 6.5 (1H, s), 7.65 (1H, s), 8.15 (1H, d), 9.5 (2H, broad).

EXAMPLE 11

28.0 g of 4-amino-5-chloro-2-methoxy benzoic acid were suspended in 300 ml of chloroform and to this, a solution of 20 g of (2S,4S)-4-amino-N-ethyl-2-hydroxymethyl pyrrolidine in 20 ml of chloroform was dropwise added, while cooling with water. After stirring for 30 minutes, the mixture was added with 2.12 g of 1-hydroxy-1H-benzotriazole monohydrate and to this, a solution of 30 g of DCC in 30 ml of chloroform was dropwise added. The combined was stirred, while cooling with water , for 14 hours and the formed DCU precipitates were removed off. The chloroform layer was washed with water and added with a dilute HCl solution. The aqueous layer was separated, washed with chloroform and neutralized with potassium carbonate. Thus treated aqueous layer was extracted with chloroform and the organic extract was washed with water, dried and concentrated under reduced pressure. To thus obtained residue, 60 ml of acetone were added and the combined was cooled with ice-water bath to precipitate crystals, which were filtered and recrystallized from acetone to obtain (2'S,4'S)-4-amino5-chloro-2-methoxy-N-(N'-ethyl-2'-hydroxymethyl pyrrolidin4'-yl) benzamide base. Yield 26.3 g M.p. 113° to 114° C.

When recrystallized from ethyl acetate or methyl ethyl ketone, said melting point was indicated 137° to 138° C.

NMR spectrum (CDCl$_3$)$\delta$(TMS, ppm): 1.05(3H, t), 1.4–3.8 (10H), 3.83 (3H, s), 4.2–4.8 (3H), 6.27 (1H, s), 8.07 (1H, s), 8.17 (1H, d).

$[\alpha]_D^{20} = -28.39$ (c=1, MeOH).

The abovesaid compound was converted into its hydrochloride in isopropyl alcohol, while blowing HCl gas therein. Water content of thus obtained hydrochloride was variable with the change in surrounding humidity, which would probably be due to its hygroscopic nature.

For example, when the hydrochloride, after being air-dried at 60° C. for overnight, was maintained in a desiccator of relative humidity of 75% for 24 hours and its water content was determined by Karl Fisher's method, it was observed that the water content was 4.00%.

M.p. 168° to 169° C. $[\alpha]_D^{20} = -11.3$ (c=1, H$_2$O),

EXAMPLE 12

2.0 g of 4-amino-5-chloro-2-methoxy benzoic acid were dissolved in 10 ml of chloroform and to this solution, 1.2 g of triethylamine were added. Thereafter, while cooling with ice-sald bath, 1.29 g of ethyl chloroformate were dropwise added and the combined was stirred at −10° C. for 1 hour. To this, a solution of 1.72 g of (2S,4S)-4-amino-N-ethyl-2-hydroxymethyl pyrrolidine in 3 ml of chloroform was dropwise added at −45° C. and while raising the temperature time to time, the mixture was reacted at −10° C. for 2 hours and then at −5° C. for additional 2 hours. Thereafter, stirring was continued until the temperature of said reaction mixture reached room temperature. The mixture was then poured into ice-water, the chloroform layer was separated and added with an aqueous dilute HCl solution. The aqueous layer was separated, washed with chloroform, neutralized with potassium carbonate and then extracted with chloroform.

The chloroform extract was washed with water, dried and concentrated to obtain an oily product. Acetone was added to this oil to obtain crystals of (2'S,4'S)-4-amino-5-chloro-2-methoxy-N-(N'-ethyl-2'-hydroxymethyl pyrrolidin-4'-yl) benzamide base. Yield 1.52 g.

This was identified with the base compound obtained in the first half of Example 11 from its M.p., NMR and $[\alpha]_D^{20}$ dates.

EXAMPLE 13

4.00 g of 4-acetylamino-5-chloro-2-methoxy benzoic acid were suspended in 20 ml of chloroform and to this suspension, 1.99 g of triethylamine were added and then, while cooling, 2.14 g of ethyl chloroformate were dropwise added. After 15 minutes later, a solution of 2.60 g of (2S,4S)-4-amino-N-ethyl-2-hydroxymethyl pyrrolidine in 3 ml of chloroform was dropwise added and reacted at room temperature for 14 hours. The reaction mixture was washed with water, added with an aqueous dilute HCl solution and an aqueous layer was separated, washed with chloroform and then neutralized with potassium carbonate. The neutralized solution was extracted with chloroform and thus obtained extract was washed with water, dried and concentrated under reduced pressure to obtain (2'S,4'S)-4-acetylamino-5-chloro-2-methoxy-N-(N'ethyl-2'-hydroxymethyl pyrrolidin-4'-yl) benzamide base as an oily product. Yield 5.68 g The oily product was then converted to hydrochloride in isopropyl alcohol while blowing HCl gas therein, which was recrystallized from ethanol. 3.39 g of purified hydrochloride were obtained. M.p. 235° to 238° C.

NMR spectrum (DMSO-d₆)δ(TMS, ppm): 1.28 (3H, t), 1.5–4.3 (9H), 2.15 (3H, s), 3.88 (3H, s), 4.7 (1H, broad), 5.5 (1H, broad), 7.77 (1H, s), 7.80 (1H, s), 8.53 (1H, d), 9.50 (1H, s), 10.9 (1H, broad).

EXAMPLE 14

To a mixture of 1.21 g of (2S,4S)-4-amino-N-ethyl-2-hydroxymethyl pyrrolidine, 0.85 g of triethylamine and 25 ml of chloroform, were added, while cooling with ice-water, 2.0 g of 4-acetylamino-5-chloro-2-methoxy benzoyl chloride and the combined was reacted under stirring for 2 hours. The reaction mixture was then washed with water, added with an aqueous dilute HCl solution and the formed aqueous layer was separated. This aqueous layer was washed with chloroform, neutralized with potassium carbonate and then extracted with chloroform. The chloroform extract was washed with water, dried and concentrated under reduced pressure to obtain (2'S,4'S)-4-acetylamino-5-chloro-2-methoxy-N-(N'-ethyl-2'-hydroxymethyl pyrrolidin-4'-yl) benzamide base as an oily product. Yield 2.90 g. This was then converted to hydrochloride in isopropyl alcohol while introducing HCl gas therein, which was recrystallized from ethanol to obtain pure hydrochloride. Yield 1.7 g.

This was identified with the hydrochloride compound obtained in Example 13 from its m.p. and NMR analytical datas.

EXAMPLE 15

To a solution of 2.0 g of (2'S,4'S)-4-acetylamino-5-chloro-2-methoxy-N-(N'-ethyl-2'-hydroxymethyl pyrrolidin-4'-yl) benzamide hydrochloride, 14 ml of methanol and 3.3 ml of water, were added 2,71 ml of aqueous 4N-NaOH solution and the combined was reacted at 65° C. for 5 hours. The reaction mixture was then concentrated under reduced pressure, added with chloroform and water, and the chloroform layer was separated. Said chloroform layer was washed with water, dried and concentrated under reduced pressure. To the residue, 16 ml of acetone were added and separated crystals were filtered to obtain (2'S,4'S)-4-amino-5-chloro-2-methoxy-N-(N'-ethyl-2'-hydroxymethyl pyrrolidin-4'-yl) benzamide base. Yield 1.05 g. This was identified with the base compound obtained in Example 11 from its m.p. and NMR analytical datas.

EXAMPLE 16

The similar experiment as stated in Example 11 was repeated excepting substituting 3.88 g of (2R,4R)-4-amino-N-ethyl-2-hydroxymethyl pyrrolidine for (2S,4S)-4-amino-N-ethyl-2-hydroxymethyl pyrrolidine, to obtain (2'R,4'R)-4-amino-5-chloro-2-methoxy-N-(N'-ethyl-2'-hydroxymethyl pyrrolidin-4'-yl) benzamide base. Yield 4.18 g NMR datas was identical with that of the base product of Example 11.

Said product was converted to its hydrochloride in 10% water-containing isopropyl alcohol, while blowing HCl gas therein.

M.p. 165° to 168° C.

$[\alpha]_D^{20} = +10.83$ (c=1, H₂O)

EXAMPLE 17

To a suspension of 0.99 g of lithium aluminium hydride in 15 ml of tetrahydrofuran, a solution of 3.03 g of (2S,4R)-4-azido 2-ethoxycarbonyl-N-ethyl pyrrolidine in 10 ml of tetrahydrofuran was dropwise added while cooling and the combined was stirred for 1 hour. Sirring was continued at room temperature for additional 2 hours, and then a mixture of 4.7 ml of aqueous 1N-NaOH solution and 33 ml of tetrahydrofuran was added to decompose excess amount of lithium aluminium hydride. After filtrating the mixture to remove undissolved substance, the filtrate was concentrated under reduced pressure to obtain (2S,4R)-4-amino-N-ethyl-2-hydroxymethyl pyrrolidine as an oily product. Yield 1.33 g.

1.33 g of the abovementioned oily product and 1.86 g of 4-amino 5-chloro-2-methoxy benzoic acid were dissolved in 8 ml of dimethylformamide and to this, were added 1.42 g of 1-hydroxy-1H-benzotriazole monohydrate and 2.0 g of DCC and the combined was stirred for 4 hours. Undissolved material was filtered and the filtrate was added with chloroform, washed with aqueous sodium bicarbonate solution and then with water, dried and concentrated under reduced pressure. Thus obtained residue was subjected to silica gel column chromatography (elution liquid: chloroformmethanol) to obtain (2'S,4'R)-4-amino-5-chloro-2-methoxy-N-(N'-ethyl-2'-hydroxymethyl pyrrolidin-4'-yl) benzamide base. Yield 2.85 g.

NMR (DMSO-d₆)δppm: 1.07 (3H, t), 1.5–3.7 (8H), 3.87 (3H, s), 4.0–4.8 (1H), 5.47 (2H, s), 6.47 (1H, s), 7.70 (1H, d) 7.80 (1H, s).

This compound was converted to its hydrochloride in isopropyl alcohol while blowing HCl gas therein. M.p. 208° to 214° C. $[\alpha]_D^{20} = -18.59°$ (c=1, H₂O)

EXAMPLE 18

The similar experiment as stated in Example 17 was repeated excepting substituting (2R,4S)-4-azido-2-ethoxycarbonyl-N-ethyl pyrrolidine for (2S,4R)-4-azido-2-ethoxycarbonyl-N-ethyl pyrrolidine to obtain (2'R,4'S)-4-amino-5-chloro-2-methoxy-N-(N'-ethyl-2'-hydroxymethyl pyrrolidin-4'-yl) benzamide base.

NMR spectrum was the same with that of the base compound of Example 17.

M.p of its hydrochloride was 208° to 210° C. $[\alpha]_D^{20} = +18.60°$ (c=1, H₂O).

EXAMPLE 19

25 g of (2'S, 4'S)-4-amino-5-chloro-2-methoxy-N-(N'-ethyl-2'-hydroxymethyl pyrrolidin-4'-yl) benzamide obtained in Example 11, 330 g of lactose and 100 g of potato starch were weighed and placed in a fluidized bed granulator.

While spraying with a 5% aqueous solution of 15 g of hydroxy propyl cellulose binder, granules were prepared. To this, were added 20 g of carboxy methyl cellulose calcium (disintegrator) and 10 g of magnesium stearate (lubricant) and the combined was mixed well. Thus obtained mixture was then subjected to a tableting machine to obtain tablets each having 100 mg weight.

Since the 3-amino-1-ethyl-5-hydroxymethyl pyrrolidine used in Example 1 was derived from 4-hydroxy-L-proline ethyl ester hydrochloride, it had a defined comformation.

This compound was synthesized as follows:

REFERENCE EXAMPLE 1

(1) A mixture of 20.0 g of 4-hydroxy-L-proline ethylester hydrochloride, 23.9 g of ethyl iodide, 25.9 g of triethylamine and 120 ml of chloroform was refluxed for 3 hours.

After cooling, the reaction mixture was washed with aqueous sodium bicarbonate solution and then with a saturated saline solution, dried over magnesium sulfate and concentrated under reduced pressure to obtain 13.7 g of N-ethyl-4-hydroxy-L-proline ethylester.

NMR (CDCl$_3$)$\delta$(TMS, ppm): 1.07 (3H, t), 1.27 (3H, t), 1.9–3.1 (5H), 3.1–3.7 (3H), 4.16 (2H, q), 4.2–4.7 (1H).

(2) To a mixture of 2.50 g of N-ethyl-4-hydroxy-L-proline ethylester, 1.76 g of triethylamine and 10 ml of chloroform were dropwise added 1.84 g of mesyl chloride while cooling with ice-water and the combined was stirred at room temperature for 2 hours and then poured into ice-water. The mixture was extracted with chloroform and the extract was washed with an aqueous sodium bicarbonate solution and then with water, dried over magnesium sulfate and concentrated under reduced pressure to obtain 3.64 g of N-ethyl-4-mesyloxy-L-proline ethylester.

NMR (CDCl$_3$)$\delta$(TMS, ppm): 1.10 (3H, t), 1.30 (3H, t), 2.1–3.1 (5H), 3.03 (3H, s), 3.3–3.8 (2H), 4.20 (2H, q), 5.26 (1H).

(3) A mixture of 3.50 g of N-ethyl-4-mesyloxy-L-proline ethylester, 1.54 g of sodium azide and 10 ml of DMF was reacted at an inner temperature of 90° C. for 4 hours and after cooling, the reaction mixture was poured into water and extracted with ethyl acetate. The extract was dried over magnesium sulfate and concentrated to obtain an oily product. This was purified by means of silica column chromatography to obtain 2.05 g of 4-azido-N-ethyl-L-proline ethylester.

NMR (CDCl$_3$)$\delta$(TMS, ppm): 1.10 (3H, t), 1.28 (3H, t), 1.8–3.5 (7H), 3.7–4.4 (1H), 4.23 (2H, q).

(4) 0.41 g of lithium aluminium hydride was suspended in 10 ml of dried THF under nitrogen stream and the suspension was cooled in ice-salt bath. To this, a solution of 1.90 g of 4-azido-N-ethyl-L-proline ethylester in 4 ml of dried THF was gently and dropwise added and then the combined was stirred for 1 hour. Thereafter, the mixture was stirred at room temperature for additional 2 hours and again cooled with ice-salt bath. To this, a mixture of 1 ml of 1N NaOH aqueous solution and 9 ml of THF was carefully and dropwise added.

After 1 hour later, the inner temperature was returned to room temperature and undissolved material was removed off. The filtrate was concentrated under reduced pressure to obtain 1.05 g of 4-amino-N-ethyl-2-hydroxymethyl pyrrolidine.

NMR (CDCl$_3$) (TMS, ppm): 1.10 (3H, t), 1.0–3.2 (10H), 3.2–3.9 (3H).

Using 4-hydroxy-L-proline ethylester hydrochloride and following the procedures as abovementioned, the following compounds were prepared:

4-amino-2-hydroxymethyl-N-methyl pyrrolidine
NMR (DMSO-d$_6$)$\delta$(TMS, ppm): 1.1–4.3 (6H), 2.25 (3H, s), 3.40 (2H, d), 3.75 (3H, s).

4-amino-N-(2-fluoroethyl)-2-hydroxymethyl pyrrolidine NMR (CDCl$_3$)$\delta$(TMS, ppm): 1.3–3.8 (10H), 2.65 (3H, s), 4.12 (1H, t), 4.90 (1H, t).

4-amino-2-hydroxymethyl-N-n-propyl pyrrolidine
NMR (CDCl$_3$)$\delta$(TMS, ppm): 0.90 (3H, t), 1.1–3.9 (12H), 2.43 (3H, s).

4-amino-2-hydroxymethyl-N-isopropyl pyrrolidine
NMR (CDCl$_3$)$\alpha$(TMS, ppm): 0.97 (3H, d), 1.10 (3H, d), 1.3–3.9 (9H), 2.57 (3H, s).

4-amino-N-benzyl-2-hydroxymethyl pyrrolidine
NMR (DMSO-d$_6$)$\alpha$(TMS, ppm): 0.7–4.3 (11H), 7.30 (5H, s), 8.27 (2H, s).

4-amino-N-diphenylmethyl-2-hydroxymethyl pyrrolidine
NMR (CDCl$_3$)$\delta$(TMS, ppm): 1.3–5.0 (8H), 2.93 (3H, s), 4.87 (1H, s), 6.9–7.7 (10H).

4-amino-2-hydroxymethyl-N-o-methoxybenzyl pyrrolidine
NMR (CDCl$_3$)$\delta$(TMS, ppm): 1.2–4.4 (13H), 3.80 (3H, s), 6.6–7.5 (4H).

4-amino-N-benzyl-2-methoxymethyl pyrrolidine
NMR (CDCl$_3$)$\delta$(TMS, ppm): 1.1–3.7 (8H), 1.77 (2H, s), 3.27 (3H, s), 3.68 (2H, q), 7.27 (5H, s).

(2S,4S)-4-amino-N-ethyl-2-hydroxymethyl pyrrolidine used (in Examples 11 to 13 was prepared, starting from 4-hydroxy-L-proline $[\alpha]_D^{20} = -76.5°$ (c=2.5, H$_2$O), as follows:

REFERENCE EXAMPLE 2

(1) To a mixture of 100 g of 4-hydroxy-L-proline$[\alpha]_D^{20} = -76.5°$ (c=2.5, H$_2$O) and 380 ml of ethanol, 109 g of thionyl chloride were dropwise added. Under heat-refluxing condition, the mixture was reacted for 4 hours and then cooled to precipitate the reaction product. 143.8 g of (2S,4R)-2-ethoxycarbonyl-4-hydroxy pyrrolidine hydrochloride were obtained as crystals. M.p. 153.5° to 154° C.

$[\alpha]_D^{20} = -29.85°$ (c=1.0, H$_2$O).

NMR (DMSO-d$_6$)$\delta$(TMS ppm): 1.25 (3H, t), 1.9–2.4 (2H), 2.8–4.7 (4H), 4.23 (2H, q).

(2) To a mixture of 10.0 g of (2S,4R)-2-ethoxycarbonyl-4-hydroxy pyrrolidine hydrochloride, 15.5 g of potassium carbonate and 50 ml of chloroform, 9.46 g of diethyl sulfate were dropwise added. At 40° C., the mixture was stirred for 4 hours and then allowed to cool, washed with water, added with an aqueous dilute HCl solution and the formed aqueous layer was separated. This aqueous layer was neutralized with potassium carbonate, extracted with chloroform and the extract was washed with water, dried and concentrated under reduced pressure to obtain (2S,4R)-2-ethoxycarbonyl-N-ethyl-4-hydroxy pyrrolidine as an oily product. Yield 8.15 g.

$[\alpha]_D^{20} = -70.80$ (c=1.06, MeOH).

NMR (CDCl$_3$)$\delta$(TMS ppm): 1.07 (3H, t), 1.27 (3H, t), 1.9–3.1 (5H), 3.1–3.7 (3H), 4.16 (2H, q), 4.2–4.7 (1H).

(3) To a mixture of 2.5 g of (2S,4R)-2-ethoxycarbonyl-N-ethyl-4-hydroxy pyrrolidine, 1.76 g of triethylamine and 10 ml of chloroform, 1.84 g of mesyl chloride were dropwise added and the combined was stirred for 2 hours. The reaction mixture was then poured into ice-water and extracted with chloroform. The chloroform extract was washed with aqueous sodium bicarbonate solution and then with water, dried and concentrated under reduced pressure to obtain (2S,4R)-2-ethoxycarbonyl-N-ethyl-4-methanesulfonyloxy pyrrolidine as an oily product. Yield 3.64 g .

$[\alpha]_D^{20} = -39.92$ (c=1.06, MeOH).

NMR (CDCl$_3$)$\delta$(TMS ppm): 1.10 (3H, t), 1.30 (3H, t), 2.1–3.1 (5H), 3.03 (3H, s), 3.3–3.8 (2H), 4.20 (2H, q), 5.26 (1H).

(4) A mixture of 3.5 g of (2S,4R)-2-ethoxycarbonyl-N-ethyl-4-methanesulfonyloxy pyrrolidine, 1.54 g of sodium azide and 10 ml of dimethylformamide was stirred at 90° C. for 4 hours. After cooling, the reaction mixture was poured into ice-water and extracted with ethyl acetate. The organic extract was washed with water, dried and concentrated under reduced pressure to obtain crude product. This was then subjected to a silica gel column chromatography (elution liq. toluene-ethyl acetate) to obtain pure (2S,4S)-4-azido-2-ethoxycarbonylN-ethyl pyrrolidine as an oily product. Yield 2.05 g.

$[\alpha]_D^{20} = -64.70$ (c=1.04, MeOH),

NMR (CDCl$_3$)δ(TMS ppm): 1.10 (3H, t), 1.28 (3H, t), 1.8–3.5 (7H), 3.7–4.4 (1H), 4.23 (2H,g).

(5) 0.41 g of lithium aluminium hydride were suspended in 10 ml of tetrahydrofuran and while cooling, a solution of 1.9 g of (2S,4S)-4-azido-2-ethoxycarbonyl-N-ethyl pyrrolidine in 4 ml of tetrahydrofuran was dropwise added thereto. After stirring at the same temperature for 1 hour, the temperature of reaction mixture was raised to room temperature and the mixture was stirred for 2 hours. To this, a mixture of 1 ml of 1N-NaOH solution and 9 ml of tetrahydrofuran was added to decompose lithium aluminium hydride and undissolved material was filtered. The filtrate was concentrated under reduced pressure to obtain (2S,4S)-4-amino-N-ethyl2-hydroxymethyl pyrrolidine. Yield 1.05 g.

$[\alpha]_D^{20} = -76.79$ (c=1.03, MeOH).

NMR (CDCl$_3$)δ(TMS ppm): 1.10 (3H, t), 1.0–3.2 (10H), 3.2–3.9 (3H).

The similar experiments as stated in Reference Example 2 were repeated using 4-hydroxy-L-proline.

$[\alpha]_D^{20} = -76.5$ (c=2.5, H$_2$O) to obtain the following compounds.

(2S,4S)-4-amino-2-hydroxymethyl-N-methyl pyrrolidine

NMR (DMSO-d$_6$)δ(TMS, ppm): 1–4.3 (6H), 2.25 (3H, s), 3.40 (2H, d), 3.75 (3H, s).

(2S,4S)-4-amino-N-(2-fluoroethyl)-2-hydroxymethyl pyrrolidine

NMR (CDCl$_3$)δ(TMS, ppm): 3–3.8 (10H), 2.65 (3H, s), 4.12 (1H, t), 4.90 1H, t).

(2S,4S)-4-amino-2-hydroxymethyl-N-n-propyl pyrrolidine

NMR (CDCl$_3$)δ(TMS, ppm): 0.90 (3H, t), 1.1–3.9 (12H), 2.43 (3H, s).

(2S,4S)-4-amino 2 hydroxymethyl-N-isopropyl pyrrolidine

NMR (CDCl$_3$)δ(TMS, ppm): 0.97 (3H, d), 1.10 (3H, d) 1.3–3.9 (9H), 2.57 (3H, s).

(2S,4S)-4-amino-N-benzyl-2-hydroxymethyl pyrrolidine

NMR (DMSO-d$_6$)δ(TMS, ppm): 0.7–4.3 (11H), 7.30 (5H, s), 8.27 (2H, s).

(2S,4S)-4-amino-N-diphenylmethyl-2-hydroxymethyl pyrrolidine

NMR (CDCl$_3$)δ(TMS, ppm): 1.3–5.0 (8H), 2.93 (3H, s), 4.87 (1H, s), 6.9–7.7 (10H).

(2S,4S)-4-amino-2-hydroxymethyl-N-(o-methoxybenzyl) pyrrolidine

NMR (CDCl$_3$)δ(TMS, ppm): 1.2–4.4 (13H), 3.80 (3H, s), 6.6–7.5 (4H).

(2S,4S)-4-amino-N-benzyl-2-methoxymethyl pyrrolidine

NMR (CDCl$_3$)δ(TMS, ppm): 1.1–3.7 (8H), 1.77 (2H, s), 3.27 (3H, s), 3.68 (2H,q), 7.27 (5H, s).

REFERENCE EXAMPLE 3

(1) 76.0 g of (2R,4R)-2-ethoxycarbonyl-4-hydroxy pyrrolidine hydrochloride obtained by the method stated in J. Org. Chem. 46, 2954 (1981) were suspended in 380 ml of chloroform and to this, were added with 94.4 g of triethylamine and then dropwise with 79.6 g of benzyloxycarbonyl chloride. While cooling with water, the combined was stirred for 7 hours and then poured into ice-water and extracted with chloroform. The chloroform extract was after-treated to obtain (2R,4R)-N-benzyloxycarbonyl-2-ethoxycarbonyl-4-hydroxy pyrrolidine as an oily product. Yield 114.5 g.

NMR (CDCl$_3$)δ(TMS, ppm): 0.9–1.5 (3H), 2.0–2.5 (2H), 3.1–4.6 (7H), 5.13 (2H,s), 7.33 (5H, s).

(2) To a mixture of 114.4 g of the oily product obtained in the preceeding para. (1) and 150 ml of pyridine, were added 89.3 g of p-toluene sulfonyl chloride and the combined was stirred at room temperature for 67 hours. The reaction mixture was poured into ice-water and extracted with toluene. The toluene extract was after-treated to obtain (2R,4R)-N-benzyloxycarbonyl-2-ethoxycarbonyl-4-p-toluenesulfonyloxy pyrrolidine as an oily product. Yield 159.5 g .

NMR (CDCl$_3$)δ(TMS, ppm): 0.9–1.5 (3H), 2.40 (3H, s), 2.2–2.6 (2H), 3.67 (2H,d), 3.8–4.6 (3H), 5.07 (2H, s), 4.8–5.9 (1H), 7.30 (5H, s), 7.52 (4H, q).

(3) 10.0 g of (2R,4R)-N-benzyloxycarbonyl-2-ethoxycarbonyl-4-(p-toluenesulfonyloxy) pyrrolidine obtained in the preceeding para. (2) were reacted with 4.7 g of anhydrous tetraethyl ammonium acetate in toluene, under refluxing condition, and the reaction mixture was allowed to cool to precipitate crystaline material. The latter was filtered and the filtrate was concentrated under reduced pressure to obtain 8.3 g of oily product. This was subjected to hydrolysis with an aqueous 1N-NaOH solution and 4.74 g of oily product thus obtained were added with 6N-HCl and refluxed for 1 hour. Thereafter, toluene was added to remove impurities and the separated aqueous layer was concentrated and acetone was added to the residue to obtain (2R,4S)-2-carboxy-4-hydroxy pyrrolidine hydrochloride. Yield 1.47 g.

1.47 g of thus obtained crystalline material were suspended in 6 ml of ethanol and the suspension was added dropwise with 1.27 g of thionyl chloride and reacted with the same. The reaction mixture was concentrated under reduced pressure and to the residue, acetone was added to obtain crystals, which were recrystallized from ethanol to obtain (2R,4S)-2-ethoxycarbonyl-4-hydroxy pyrrolidine hydrochloride. Yield 1.08 g M.p. 153° to 153.5° C.

$[\alpha]_D^{20} = +29.78$ (c=1 , H$_2$O).

NMR spectrum of this product was the same with that of Reference Example 2 (1).

(4) The similar experiments as stated in Reference Example (2) were repeated excepting using 8.99 g of (2R,4S)-2-ethoxycarbonyl-4-hydroxy pyrrolidine hydrochloride obtained in the preceeding para. (3), to obtain 7.54 g of (2R,4S)-2-ethoxycarbonyl-N-ethyl-4-hydroxy pyrrolidine NMR datas were identical with those of the compound obtained in Reference Example 2 (2).

(5) The similar experiments as stated in Reference Example 2 (3) were repeated excepting using 7.54 g of (2R,4S)-2-ethoxycarbonyl-N-ethyl-4-hydroxy pyrrolidine obtained in the preceeding para. (4), to obtain (2R,4S)-2-ethoxycarbonyl-N-ethyl-4-methanesulfonyloxy pyrrolidine. Yield 9.87 g NMR spectrum of this compound was the same with that of the compound obtained in Reference Example 2 (3).

(6) The similar experiments as stated in Reference Example 2 (4) were repeated excepting using 9.87 g of (2R,4S)-2-ethoxycarbonyl-N-ethyl-4-methanesulfonyloxy pyrrolidine obtained in the preceeding para. (5), to obtain (2R,4R)-4-azido-2-ethoxycarbonyl-N-ethyl pyrrolidine. Yield 6.61 g.

$[\alpha]_D^{20} = +63.70$ (c=1.0, MeOH).

NMR spectrum of this compound was the same with that of the compound obtained in Reference Example 2 (4).

(7) The similar experiments as stated in Reference Example 2 (5) were repeated excepting using 6.61 g of (2R,4R)-4-azido-2-ethoxycarbonyl-N-ethyl pyrrolidine obtained in the preceeding para. (6), to obtain (2R,4R)-4-amino-N-ethyl-2-hydroxymethyl pyrrolidine. Yield 3.88 g.

NMR spectrum of this compound was the same with that of the compound obtained in Reference Example 2 (5).

REFERENCE EXAMPLE 4

(1) 56.34g of (2S,4S)-N-benzyloxycarbonyl-2-carboxy-4-hydroxy pyrrolidine obtained by the method stated in J. A. C. S. 79, 185 (1957) and 1280 ml of 6N-HCl were heat-refluxed for 30 minutes. The rection mixture was concentrated and added with acetone to precipitate crystals. The crystals were separated. Yield 35.19 g.

Into a solution of 5 g of thus obtained crystals in 25 ml of ethanol, 6.49 g of thionyl chloride were dropwise added and the combined was heat-refluxed for 4 hours.

The rection mixture was concentrated, added with acetone and allowed to cool. The precipitates were filtered to obtain (2S,4S)-2-ethoxycarbonyl-4-hydroxy pyrrolidine hydrochloride. Yield 3.38 g M.p. 152° to 154.5° C.

$[\alpha]_D^{20} = -20.34°$ (c=1, $H_2O$).

NMR (DMSO-$d_6$)δ(ppm): 1.27 (3H,t), 2.0–2.7 (2H), 3.23 (2H, d), 4.22 (2H, q), 4.2–4.8 (2H), 5.50 (1H, broad), 9.77 (2H, broad).

(2) To a suspension of 12 g of (2S,4S)-2-ethoxycarbonyl-4-hydroxy pyrrolidine hydrochloride obtained in the preceeding para. (1) in 60 ml of chloroform, were added 12.42 g of triethylamine and the combined was added with 17.22 g of ethyl iodide and heat-refluxed for 4 hours. The reaction mixture was after-treated to obtain (2S,4S)2-ethoxycarbonyl-N-ethyl-4-hydroxy pyrrolidine as an oily (product Yield 9.55 g.

IR (cm$^{-1}$) 3392 (OH), 1734 (C=O).

NMR (DMSO-$d_6$)δ(ppm): 1.13 (3H, t), 1.33 (3H, t), 1.7–3.5 (8H), 4.0–4.6 (1H), 4.23 (2H, q).

(3) The similar experiments as stated in Reference Example (3) and 2 (4) were repeated excepting using 9.55 g of (2S,4S)-2-ethoxycarbonyl-N-ethyl-4-hydroxy pyrrolidine obtained in the preceeding para. (2) to obtain (2S,4R)-4-azido-2-ethoxycarbonyl-N-ethyl pyrrolidine as an oily product. Yield 5.29 g.

8 $\alpha]_D^{20} = -64.64°$ (c=1, MeOH).

IR (cm$^{-1}$): 2103 (azido).

NMR (CDCl$_3$)δ(ppm): 1.10 (3H, t), 1.28 (3H, t), 1.8–3.2 (5H), 3.2–3.7 (2H, m) 3.9–4.5 (1H), 4.20 (2H, q).

REFERENCE EXAMPLE 5

(1) Using (2R,4R)-2-ethoxycarbonyl-4-hydroxy pyrrolidine hydrochloride obtained by the method described in J. O. C. 46, 2954 (1981), the similar experiment as stated in Reference Example 4(2) was repeated to obtain (2R,4R)-2-ethoxycarbonyl-N-ethyl-4-hydroxy pyrrolidine.

IR and NMR spectrum of this compound were identical with those of the compound obtained in Reference Example 4(2).

(2) Using (2R,4R)-2-ethoxycarbonyl-N-ethyl-4-hydroxy pyrrolidine obtained in the preceeding para. (1), the similar experiments as stated in Reference Example 2(3) and 2(4) were repeated to obtain (2R,4S)-4-azido-2-ethoxycarbonyl-N-ethyl pyrrolidine.

$[\alpha]_D^{20} = +64.00°$ (c=1, MeOH).

IR and NMR spectrum of this compound were identical with those of the compound obtained in Reference Example 4(3).

EFFECTS OF THE INVENTION

The present benzamide derivatives each has the properties for promoting activity to digestive tract and especially to stomach.

Among them, (2'S,4'S)-4-amino-5-chloro-2-methoxy-N-(N'-ethyl-2'-hydroxymethyl pyrrolidin-4'-yl) benzamide, one of the optical isomers, showed specifically excellent effect in mouse.

In mouse tests, stomach excretion promoting rates of the compounds obtained in Examples 11 to 15 were 21.1% at the dosis of 0.3 mg/kg, 31.6% at 1 mg/kg and 43% at 3 mg/kg. The effects of the compounds obtained in Examples 1 to 10 and Examples 11, 16, 17 and 18 are shown below in Table 1 and Table 2.

TABLE 1

| Example | Promoting rate (%) of stomach excretion in mouse at 3 mg/kg (p.o.) | prevention of vomiting in dog at 0.1 mg/kg (s.c.) |
|---|---|---|
| 1 | 42 | no |
| 2 | 37 | no |
| 3 | 36 | no |
| 4 | 24 | yes |
| 5 | 18 | yes |
| 6 | 17 | yes |
| 7 | 13 | no |
| 8 | 17 | no |
| 9 | 24 | no |
| 10 | 25 | no |
| MCP | 33 | yes |

MCP ... Metoclopramide hydrochloride

TABLE 2

| Example | stereo-specf. struct. | Promoting rate (%) of stomach excretion in mouse at 3 mg/kg (p.o.) | prevention of vomiting in dog at 0.1 mg/kg (s.c.) |
|---|---|---|---|
| 11 | 2'S,4'S | 42.8 | no |
| 16 | 2'R,4'R | 20.0 | no |
| 17 | 2'S,4'R | 10.6 | no |
| 18 | 2'R,4'S | 22.3 | no |

Stomach excretion activities of Metoclopramide and Cisapride in mouse are as follows:

| | | |
|---|---|---|
| Metoclopramide | 0.3 mg/kg | 8.3% |
| | 1.0 | 9.4 |
| | 3.0 | 25.0 |
| | 10.0 | 34.8 |
| | 30.0 | 49.2 |
| Cisapride | 0.3 | 8.3 |
| | 1.0 | 29.1 |
| | 3.0 | 32.5 |

What is claimed is:
1. A benzamide derivative represented by the formula:

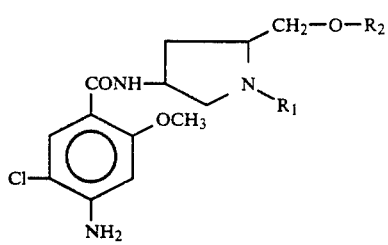

in which $R_1$ is hydrogen atom, lower alkyl, halogen substituted lower alkyl or aralkyl group; $R_2$ is hydrogen atom or lower alkyl group.

2. A benzamide derivative represented by the formula:

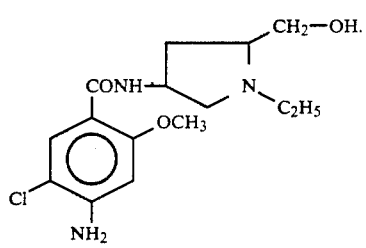

3. A 2′S,4′S-benzamide derivative represented by the formula:

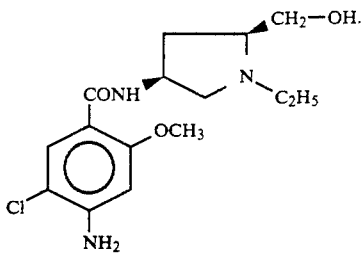

4. A pharmaceutical composition comprising an effective amount for promoting activities of the gastrointestinal tract of derivative of the formula:

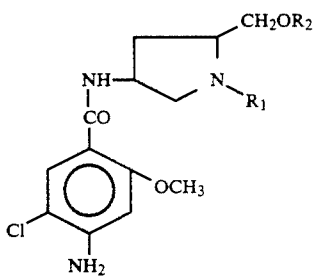

or its acid addition salt,
in which $R_1$ is hydrogen atom, lower alkyl, halogen substituted lower alkyl or aralkyl group;
$R_2$ is hydrogen atom or lower alkyl group, and pharmaceutically acceptable carriers.

5. A method for promoting activity of the gastrointestinal tract which comprises administering an effective amount of a benzamide derivative as defined in claim 1.

* * * * *